United States Patent
Rapp et al.

(10) Patent No.: US 7,111,495 B2
(45) Date of Patent: Sep. 26, 2006

(54) SENSOR BASED ON SURFACE COMPONENTS WITH CAPACITATIVE COUPLING OF THE HIGH FREQUENCY CONNECTIONS

(75) Inventors: Michael Rapp, Eppelheim (DE); Achim Voigt, Eggenstein-Leopoldshafen (DE)

(73) Assignee: Forschungszentrum Karlsruhe, Karlsruhe (DE)

( * ) Notice: Subject to any disclaimer, the term of this patent is extended or adjusted under 35 U.S.C. 154(b) by 42 days.

(21) Appl. No.: 10/965,362

(22) Filed: Oct. 14, 2004

(65) Prior Publication Data

US 2005/0044956 A1    Mar. 3, 2005

Related U.S. Application Data

(63) Continuation-in-part of application No. PCT/EP03/03717, filed on Apr. 10, 2003.

(30) Foreign Application Priority Data

May 15, 2002   (DE) ................ 102 22 068

(51) Int. Cl.
   *G01N 29/02*   (2006.01)
   *G01N 29/24*   (2006.01)
(52) U.S. Cl. ................... 73/24.01; 73/24.06
(58) Field of Classification Search ........... 73/24.01, 73/24.06, 31.05
See application file for complete search history.

(56) References Cited

U.S. PATENT DOCUMENTS

| 4,296,347 | A | * | 10/1981 | Weirauch | ........... 310/313 B |
| 5,003,822 | A | * | 4/1991 | Joshi | ........... 73/204.23 |
| 5,817,922 | A | * | 10/1998 | Rapp et al. | ........... 73/24.06 |
| 6,314,791 | B1 | * | 11/2001 | Rapp et al. | ........... 73/24.06 |

FOREIGN PATENT DOCUMENTS

DE       196 19 311 A1    12/1996
WO       WO 01/61336 A1    8/2001

OTHER PUBLICATIONS

Patent Abstracts of Japan, Publication No. 2000223989 of Nov. 8, 2000Surface Acoustic Wave Device
Freudenberg, J. et al., A SAW Immunosensor for Operation in Liquid Using a $SiO_2$ Protective Layer, Sensors and Actuators B, vol. 76, 2001, 147-151.

* cited by examiner

*Primary Examiner*—Daniel S. Larkin
(74) *Attorney, Agent, or Firm*—Klaus J. Bach

(57) ABSTRACT

In a sensor on the basis of surface wave components disposed in a housing with at least one surface wave component, a fluid channel and conductors for high frequency signals, the conductors are connected to coupling capacitors with capacitive coupling surface areas which are arranged opposite each other on the housing and the surface wave equipment and closely adjacent one another so that high frequency signals can be transmitted to, and from, the surface wave components.

4 Claims, 2 Drawing Sheets

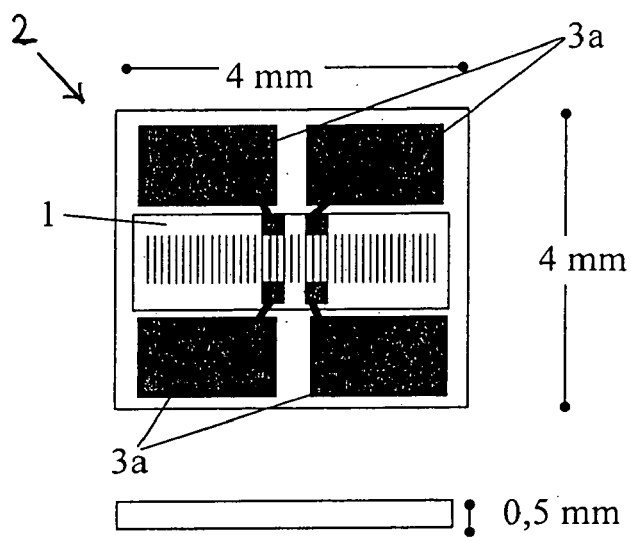
Fig. 1
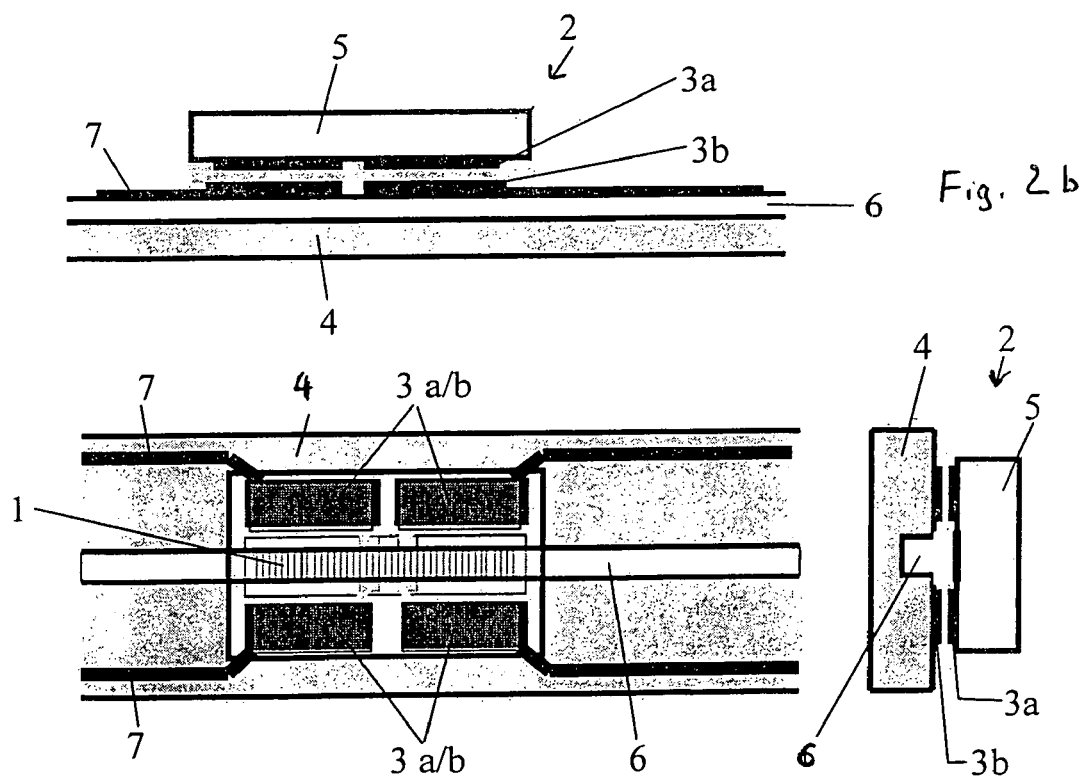
Fig. 2a
Fig. 2b
Fig. 2c

SENSOR BASED ON SURFACE COMPONENTS WITH CAPACITATIVE COUPLING OF THE HIGH FREQUENCY CONNECTIONS

This is a Continuation-In-Part application of international application PCT/EP03/03717 filed Apr. 10, 2003 and claiming the priority of German application 102 22 068.9 filed 15 May 2002.

BACKGROUND OF THE INVENTION

The invention relates to a sensor based on surface wave components, consisting of a housing with at least one surface component, a fluid channel, and conduits for conducting high frequency signals to, and from, the housing as it is known from DE 44 17 170.

In the field of sensors, piezoelectric high frequency components, such as bulk oscillators, surface wave resonators, surface work delay conduits, and filters on a quartz or ceramic basis, are electrically contacted by way of bond or weld joints. The bond wires are often disposed in areas of the sensor which carry fluids and generate additional noise as a result of vibrations, corrosion, and different materials at the point of contacts. They require space for the provision of bond loops and contacts and they cause signal delays by needed components and fixing cement.

R. Steindl et al.: SAW Delay Lines for Wirelessly Requestable Conventional Sensors, Proc. IEEE Ultrasonic Symposium, discloses SAW components which are controlled passively by transponders with antennas by way of electromagnetic waves.

J. Freudenberg et al.: A SAW immuno-sensor for operating in liquid using a $SiO_2$ protection layer, Sensors and Actuators B 76 (2001) 147–151 discloses a SAW chip which is coupled by induction via a current loop. The high frequency coupling by way of antenna loops however requires a relatively large space on the surface of the sensor chip. The coupling must be placed mechanically accurately in order to compensate for insertion damping changes at different antenna distances. In addition, the sender and receiver antenna impedances must be adapted for which additional component changes and installation damping changes are necessary. The complete signal is highly delocalized by the inductive part of the antenna coupling. Because of the large amount of over-recording consequently different coupling structures cannot be arranged in a spatially tight manner.

It is the object of the present invention to provide a sensor of the type described above which however is simple in design and small in size.

SUMMARY OF THE INVENTION

In a sensor based on surface wave components disposed in a housing with at least one surface wave component, a fluid channel, and conductors for high frequency signals, the conductors are connected to coupling capacitors with capacitive coupling surface areas which are arranged opposite each other on the housing and the surface wave equipment and closely adjacent one another so that high frequency signals can be transmitted to, and from, the surface wave components.

With the capacitive coupling areas on the surface wave component (sensor) and the connection-base plate (conductor plate), the high frequency can be transmitted in a contact-free manner. The sensor surface can be provided all over with thin protection or sensor layers without a need for an ohmic contact. Furthermore, the fluid-conducting space can be provided in the coupling conductor plate which provides for small sample volumes.

On the sensor chip capacitive coupling surface areas are present which are disposed opposite the respective receiver surface areas on the conductor plate in a planar and parallel arrangement. The distance therebetween or the thickness of the dielectric between the coupling surfaces is determined by the sensor coating and is a few 100 nm.

With the capacitive coupling, the system can be relatively small without causing undesired signal transfers within a sensor array.

In biosensor engineering, it is important to be able to operate with minimal amounts of protein in order to keep the expenses for the analysis low.

An important advantage of the sensor, according to the invention, resides in the reduction of the sample volume and the avoidance of cementing materials as they are normally used in the assembly of conventional SAW components and the sealing of a measuring cell with polymer materials. Examinations have shown that they are responsible for signal delays. All requirements can effectively be obtained only if the high frequency is transmitted by a capacitive coupling.

The sensor has the following additional advantages:

The coupling of the sensor is contact-free. The whole sensor can be coated with any insulating material (polymer).

The sensor is mechanically stable since it is disposed on the conductor plate.

A fluid can be conducted in the space between the capacitive coupling surfaces within the conductor plate.

No attachment cement is needed for bonded components.

There is a good thermal coupling with the conductor plate.

A multitude of coupling areas can be established in a small space.

A capacitively coupling test adapter with internal gas passage for a 433 MHz SAW gas sensor array was developed. In this case, the sample volume was reduced from 1300 μl to 60 μl and, because of the elimination of mounting cement a substantial increase in the signal dynamics was obtained.

An exemplary embodiment of the invention will be described below on the basis of the accompanying drawings.

BRIEF DESCRIPTION OF THE DRAWINGS

FIG. 1 shows schematically a sensor with coupling condensers and a central resonator structure, FIG. 2a shows a sensor arrangement in a top view, FIG. 2b shows the sensor arrangement in a vertical longitudinal cross-sectional view, FIG. 2c shows the sensor arrangement in a vertical transverse cross-sectional view.

DESCRIPTION OF A PREFERRED EMBODIMENT

Figure 3:
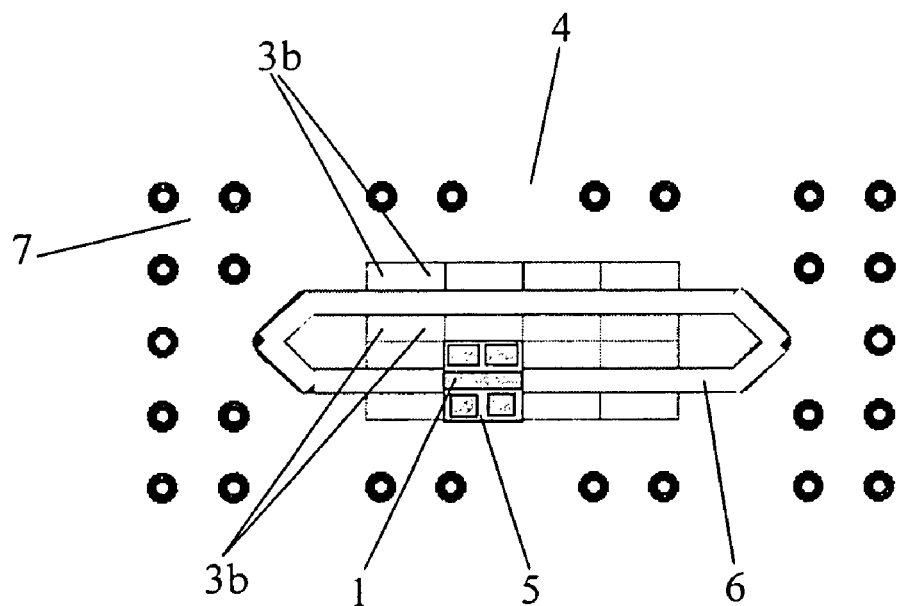
FIGS. 3 and 4 show the arrangement of sensors on the conductor plate.

FIG. 1 shows a surface wave component structure 2 with typical exemplary dimensions indicated in the figure. It includes four capacitive coupling areas 3a with a central resonator structure 1, which is galvanically connected to the coupling areas 3a for the transfer of high frequency signals.

The connections are not shown in detail.

FIGS. 2a–2c show the arrangement of a sensor 5 on a support plate 4 with coupling surfaces 3a, 3b, and a fluid channel 6 in three different views. The support plate 4 includes the fluid channel 6 and supports the conductor straps 7 with the coupling surfaces 3b. Opposite thereof are the coupling surfaces 3a and the sensor 5, which are both surrounded by a sensor coating. The frame which is cemented to the support plate 4 in a gas tight manner and which fittingly extends around the sensor 5 and the area seal which seals the frame on the top are not shown.

FIG. 3 shows the top side of a support plate with a 1 mm deep and 1.2 mm wide gold-coated groove forming a gas channel 6, wherein the gas channel 6 includes two symmetrically arranged sections. Of the eight sensors 5, only one is shown. The coupling surfaces 3b for the ground connection are shown here as a common area.

Figure 4:
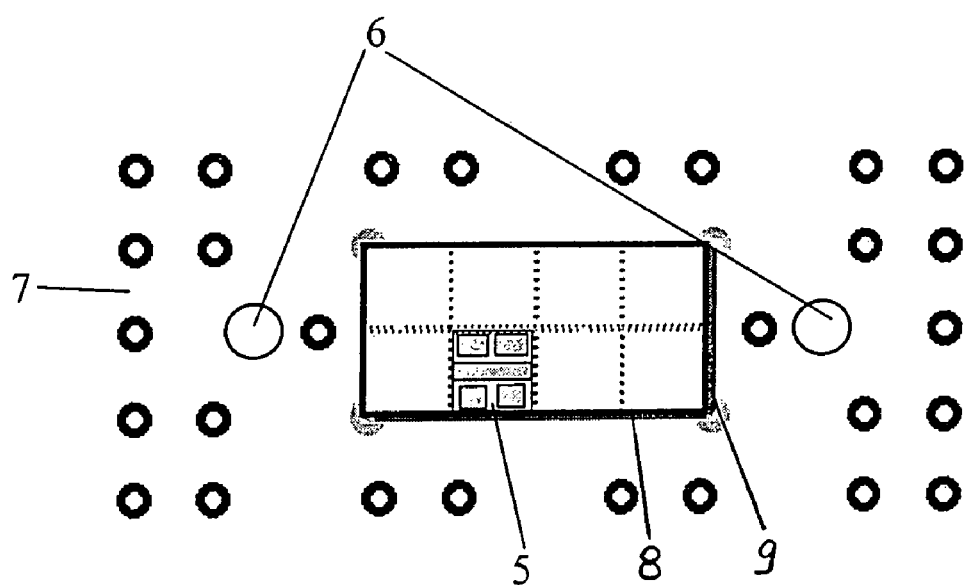

FIG. 4 shows the mounting frame 8 for the SAW sensors 5 with accurately fitted grooves with gas channels and passages to be cemented onto the support plate 4.

The eight sensors are placed with their sensitive surfaces facing downwardly onto the frame which is cemented onto the support plate 4 in such a way that the sensor surfaces are disposed over coupling surface areas. The sensors are pressed into engagement with the frame by an elastic compound seal structure forming a housing 9 for example of nitrile-butadiene rubber (NBR) and TEFLON® (polytetrafluoroethylene), so that they are in firm contact with the coupling surface areas 3b. In this way, the sensors are sealed and a predetermined engagement pressure of the coupling surface areas is obtained reducing the size of any gap.

What is claimed is:

1. A sensor-based surface wave component structure (2) comprising a housing with a support plate (4) consisting of a modified conductor plate supporting a frame (8) connected to the conductor plate (4) in a gas-tight manner, at least one surface wave component (5) disposed on the support plate (4), said support plate (4) including a fluid channel, and carrying conductors for the passage of high frequency signals, coupling capacitors disposed on the support plate (4) and on the surface wave component (5), and having capacitive coupling areas (3a, 3b) disposed opposite one another on the surface wave component (5) and, respectively, on the support plate (4), said conductors being connected to the coupling areas (3a, 3b) for the transmission of high frequency signals to, and from, the at least one surface wave components (5).

2. A sensor according to claim 1, wherein the housing includes a cover and an area seal is arranged between the support plate (4) and the cover, and is pressed onto the frame thereby fixing the at least one surface wave component (5) to the frame.

3. A sensor according to claim 1, wherein the frame surrounds the at least one surface wave component (5) in a form-fitting manner.

4. A sensor according to claim 1, wherein the housing contains eight surface wave components (5) which are arranged in two groups along a branched fluid channel (6).

* * * * *